United States Patent [19]

Wippler et al.

[11] Patent Number: 5,069,672
[45] Date of Patent: Dec. 3, 1991

[54] REUSABLE DIAPER

[76] Inventors: Heather Wippler, 29 Hartsfield Drive, Bowmanville, Ontario, L1C 4A6, Canada; Leopole Nolet, 2951 Highway 7 West, Unit 4, Concord, Ontario, L4K 1W3, Canada

[21] Appl. No.: 586,149

[22] Filed: Sep. 21, 1990

[30] Foreign Application Priority Data

Jun. 21, 1990 [CA] Canada .................................. 2019560

[51] Int. Cl.⁵ ........................ A61F 13/15; A61F 13/20
[52] U.S. Cl. .................................. 604/385.1; 604/387; 604/395; 604/398; 604/400
[58] Field of Search ....................... 604/385.1, 391, 378, 604/385.2, 375, 393, 384, 387, 395, 398, 400

[56] References Cited

U.S. PATENT DOCUMENTS

| | | | |
|---|---|---|---|
| 4,475,912 | 10/1984 | Coates | 604/385.1 |
| 4,576,601 | 3/1986 | Brain | 604/398 |
| 4,728,326 | 3/1988 | Gilles | 604/385.1 |
| 4,834,737 | 5/1989 | Khan | 604/385.2 |
| 4,961,736 | 10/1990 | McCloud | 604/385.1 |
| 4,973,325 | 11/1990 | Sherrod et al. | 604/385.1 |
| 5,019,068 | 5/1991 | Perez et al. | 604/395 X |

Primary Examiner—David J. Isabella
Assistant Examiner—Elizabeth M. Burke
Attorney, Agent, or Firm—Mason, Fenwick & Lawrence

[57] ABSTRACT

There is provided a new and useful reusable diaper comprising inner and outer substantially rectangular layers of absorbent material, a liquid impervious layer between the inner and outer layers, and first and second pockets on the inner layer, and wherein the open sides of the first and second pockets are oriented toward each other.

12 Claims, 2 Drawing Sheets

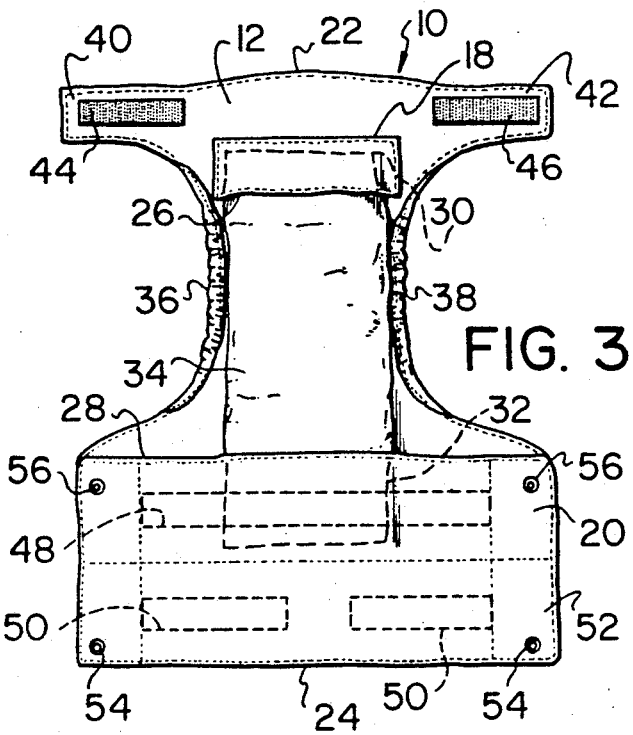
FIG. 3
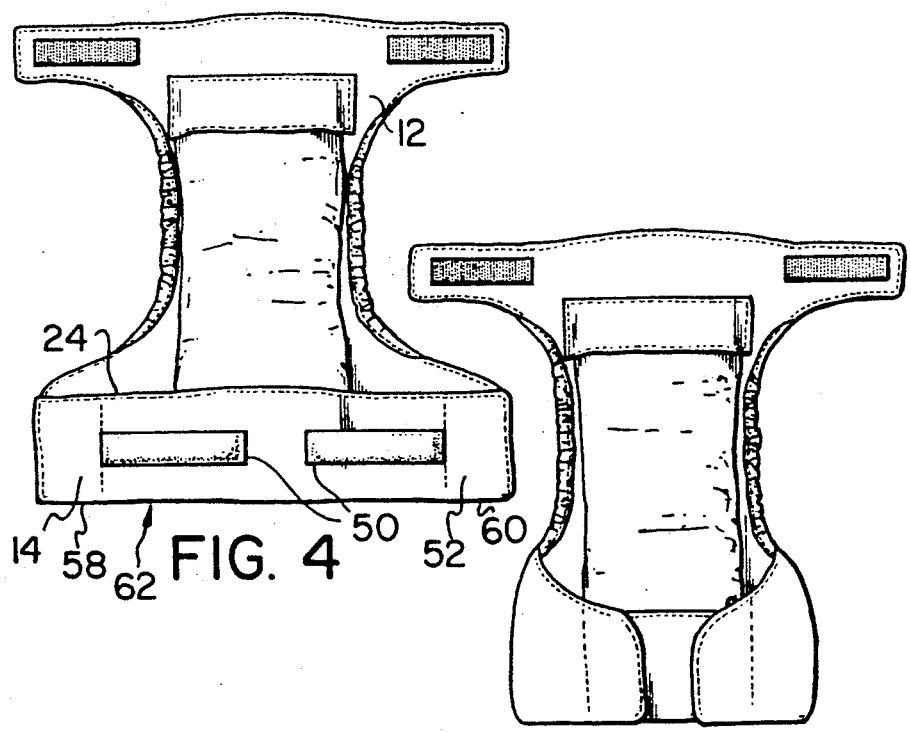
FIG. 4
FIG. 5

REUSABLE DIAPER

BACKGROUND OF THE INVENTION

Primarily because of perceived substantial environmental problems arising out of the difficulty of disposal of single use disposable diapers, a significant need has arisen for diapers which offer many of the advantages of disposables but which are reusable.

A significant problem which mitigates against the use of reusable diapers is the difficulty encountered in washing and drying. In order to equal the performance of disposable diapers, a reusable one must comprise several absorbent layers and should as well be impervious to moisture. When the various layers have been built up the product tends to be difficult to properly wash because of the number and arrangement of the multiple layers. There is therefore a significant possibility that the diaper will not be properly cleaned.

Once the washing has been accomplished, the drying step also presents problems. For the same reasons, namely, bulk and number of layers, adequate drying may take a very long time in a domestic clothes dryer. This is very undesirable for various reasons, including wear and tear on the dryer and high energy costs. Further, the availability of the dryer for other clothing items is affected.

Recently, a substantial number of reusable diapers have begun to appear in the marketplace. While each of these may offer advantages over the others, and while claims may be made in respect of washing and drying, a completely satisfactory diaper is not yet available.

Against this background the present invention provides a diaper which offers advantages in washing and drying and in addressing other needs.

PRIOR ART

A very wide variety of diapers have been patented, but none are known which provide the structure or advantages of the present case. The following patents are of interest.

U.S. Pat. No. 4,728,326, granted Mar. 1, 1988 to Gilles, provides a diaper which is of adjustable size, the adjustment affected by folding over and restraining one end of a diaper.

U.S. Pat. No. 4,773,906, granted Sept. 27, 1988, to Krushel, illustrates a diaper in which an absorbent insert is sewn at its ends to the inside of the diaper proper.

SUMMARY OF THE INVENTION

A diaper has now been developed which provides advantages aimed at reducing the problems of earlier such diapers. A liquid impervious layer is retained between two soft absorbent layers, and provision is made for the use of a removable absorbent insert.

Thus, the invention provides a reusable diaper comprising inner and outer substantially rectangular layers of absorbent material, a liquid impervious layer between the inner and outer layers, and first and second pockets on the inner layer, and wherein the open sides of the first and second pockets are oriented toward each other.

In a preferred embodiment the pockets are located toward respective first and second ends of the inner layer of the diaper and the open sides of the pockets are perpendicular to the long sides of the rectangular layers.

In a further preferred embodiment the diaper includes means for adjusting its length, said means comprising at least two said strip fasteners adjacent an adjustment end of the diaper spaced from each other longitudinally of the diaper.

BRIEF DESCRIPTION OF THE DRAWINGS

These and other objects and advantages of the invention will become apparent upon reading the following detailed description and upon referring to the drawings in which:

FIG. 3 is a plan view of the "inner" side of a further diaper according to the invention; and FIGS. 4 and 5 illustrate the diaper of FIG. 3 in folded configuration.

Figure 1:
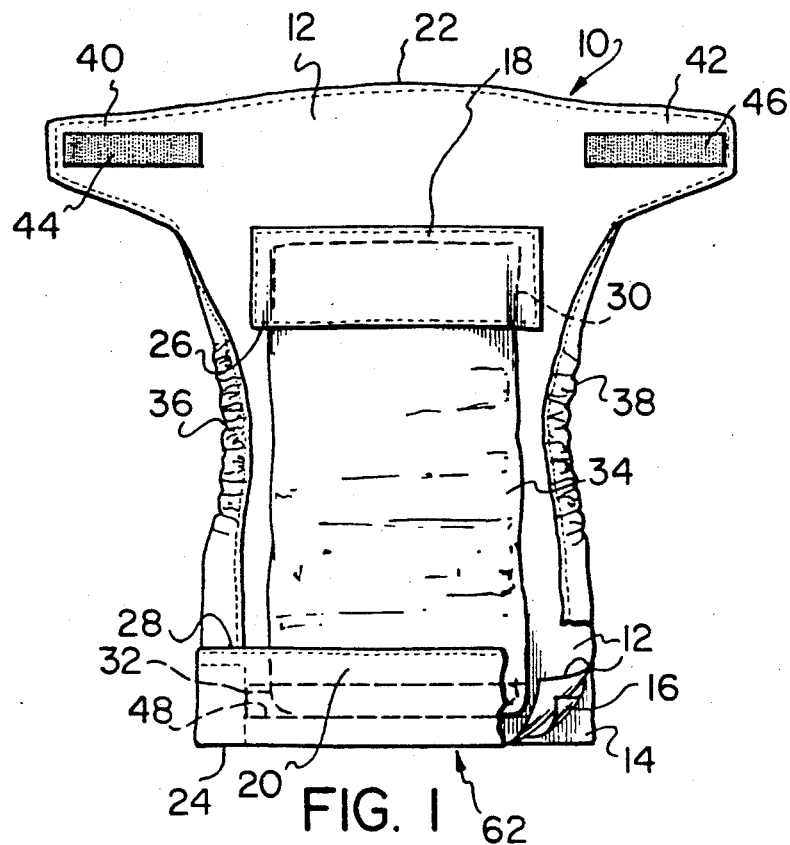
FIG. 1 is a plan view partially cut away of the "inner" side of a diaper according to the invention.
Figure 2:
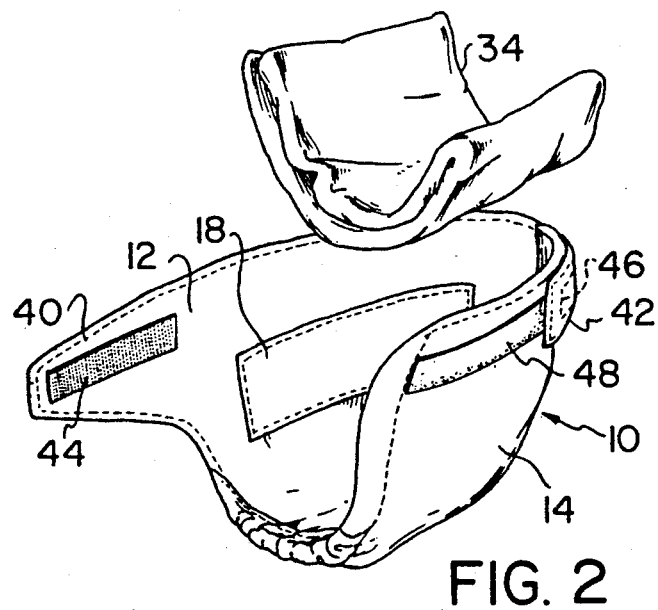
FIG. 2 is a partly exploded and partly unfolded perspective of the diaper of FIG. 1 folded into the "in use" configuration.

While the invention will be described in conjunction with illustrated embodiments, it will be understood that it is not intended to limit the invention to such embodiments. On the contrary, it is intended to cover all alternatives, modifications and equivalents as may be included within the spirit and scope of the invention as defined by the appended claims.

DETAILED DESCRIPTION OF THE PREFERRED EMBODIMENTS

A reusable diaper 10 comprises soft fabric inner layer 12 and outer layer 14. An intermediate liquid impervious layer 16 is secured between inner layer 12 and outer layer 14.

The three layers 12, 14 and 16 are preferably of the same shape and are secured together by stitching around their periphery.

First and second pockets 18 and 20 are secured toward first and second ends 22 and 24 respectively of diaper 10. The pockets are stitched along three sides and have their respective open sides 26 and 28 oriented perpendicular to the longitudinal axis of diaper 10 and facing each other. The specific shape of the pockets is not of particular importance, although a basic rectangular shape is preferred.

In use the pockets 18 and 20 preferably have inserted therein the respective ends 30 and 32 of an absorbent insert 34. The insert 34 is preferably formed by folding a conventional cloth diaper to the appropriate size.

In a preferred configuration the diaper 10 includes concave arcuate sides 36 and 38 which are gathered and elasticized. The sides are preferably elasticized by simply stitching a stretched elastic strip along the sides in the area where the elasticized section is required.

As well, the preferred configuration includes a pair of outwardly extending tabs 40 and 42 at the end 22 of diaper 10.

The diaper 10 is preferably provided with strip fasteners of the hook and loop type. In that regard the parts 44 and 46 of the strip fasteners are secured at the end 22 of diaper 10 on tabs 40 and 42. The second part 48 of the strip fasteners is secured adjacent the opposite end 24 of diaper 10 and on the side of the diaper appropriate to obtain the necessary mating of parts 44 and 46 with part 48. Thus, for example, the parts 44 and 46 are preferably on the inner layer 12 of diaper 10, and the second part 48 is preferably on the outer layer 14 of diaper 10.

In a preferred embodiment the diaper 10 is provided with means for adjusting the length of the diaper. Thus, as illustrated in FIG. 3-5, additional strip fastener second parts 50 are secured to an extended part 52 of the end 24 of diaper 10. The user can then choose to utilize either the parts 48 or 50 with the parts 44 and 46 to adjust the diaper size.

Where the diaper is used on a smaller baby, such that the part 48 is used for fastening, means comprising snap fasteners comprising first and second parts 54 and 56 respectively are provided for securing the end 24 of diaper 10 in a folded over position, as illustrated in FIG. 4. In use the outer edges 58 and 60 of folded section 62 are themselves preferably folded over as illustrated in FIG. 5 to cover the parts 50 to thereby prevent skin irritation.

It will be clear that the use of the insert 34 to form a major part of the absorbency of the diaper 10 will greatly facilitate cleaning the diaper 10. Furthermore, since the insert itself preferably comprises multiple layers of a folded material, the insert can be unfolded for cleaning and thus much more efficiently washed and dried.

It is preferred that the two "male" strips 42 and 44 be joined for laundering. This avoids the problem of multiple diapers becoming interconnected while laundering. Since end 22 is the thinner end of the diaper, this joining does not create drying problems.

Thus it is apparent that there has been provided in accordance with the invention an improved diaper that fully satisfies the objects, aims and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the invention.

What we claim as our invention:

1. A reusable diaper comprising:
   (a) inner and outer substantially rectangular layers of absorbent material;
   (b) a liquid impervious layer between said inner and outer layers;
   (c) opposed first and second pockets on said inner layer, said pockets having open sides oriented toward each other; and
   (d) at least one absorbent insert in an area between said pockets, said insert having opposite ends inserted into respective ones of said open sides of said pockets, and said insert comprising a single sheet folded along a fold line to form at least two layers, said layers secured to each other only along said fold line.

2. The diaper of claim 1, wherein said pockets are located toward respective first and second ends of said inner layer and the open sides of said pockets are perpendicular to the long sides of said rectangular layers.

3. The diaper of claim 2 including strip fasteners adjacent the ends thereof which are adapted to mate when said diaper is folded over end to end.

4. The diaper of claim 3 including means for adjusting the length of said diaper, said means comprising at least two said strip fasteners adjacent an adjustment end of said diaper spaced from each other longitudinally of said diaper.

5. The diaper of claim 4 including fastening means associated with said adjustment end whereby to selectively maintain said end in a folded-over condition to thereby shorten said diaper.

6. The diaper of claim 5 wherein said fastening means comprises snap fasteners.

7. The diaper of claim 2 wherein at least a part of the longitudinal edges of said diaper have a concave arcuate shape.

8. The diaper of claim 2 wherein at least a part of the longitudinal edges of said diaper include a gathered section and elastic means within said gathered section.

9. The diaper of claim 1 wherein said impervious layer substantially conforms in shape to said inner and outer layers, all said layers secured together along their edges.

10. The diaper of claim 2 wherein each said pocket comprises a strip of absorbent material stitched on three sides to said inner layer.

11. The diaper of claim 1 wherein one end of said diaper includes at least two strip fasteners, one extending beyond each side of said rectangular layers, and the other end of said diaper includes at least one strip fastener substantially within the boundaries of said rectangular layers.

12. The diaper of claim 1 wherein said single layer is a conventional rectangular cloth diaper.

* * * * *